United States Patent [19]

Chwang et al.

[11] Patent Number: 4,749,517

[45] Date of Patent: Jun. 7, 1988

[54] ETHOXYLATED JOJOBA OIL

[75] Inventors: Willy K. Chwang; James F. Stephens, both of Baltimore; Ronald W. Kreis, Ellicott City, all of Md.

[73] Assignee: Alcolac, Inc., Baltimore, Md.

[21] Appl. No.: 8,334

[22] Filed: Jan. 29, 1987

[51] Int. Cl.$^4$ ............... C10M 107/20; C10M 107/22

[52] U.S. Cl. ................. 252/56 S; 252/52 A; 252/56 R; 424/195.1; 514/844; 514/847

[58] Field of Search ............ 252/56 S, 52 A; 424/195.1; 514/844, 847

[56] References Cited

U.S. PATENT DOCUMENTS

| | | | |
|---|---|---|---|
| 4,067,817 | 1/1978 | Sturwold | 252/56 S |
| 4,075,393 | 2/1978 | Sturwold | 252/56 R |
| 4,108,785 | 8/1978 | Sturwold | 252/56 R |
| 4,130,495 | 12/1978 | Wisniak et al. | 252/48.6 |
| 4,370,319 | 1/1983 | Chapin et al. | 424/184 |
| 4,410,517 | 10/1983 | Stillman | 424/195 |
| 4,525,344 | 6/1985 | Tutsky | 424/73 |
| 4,551,332 | 11/1985 | Stillman | 424/195.1 |
| 4,581,230 | 4/1986 | Grollier et al. | 424/74 |
| 4,585,656 | 4/1986 | Rosenthal et al. | 424/195.1 |
| 4,595,586 | 6/1986 | Flom | 424/59 |
| 4,664,821 | 5/1987 | Arndt | 252/56 R |
| 4,664,914 | 5/1987 | Stillman | 424/195.1 |
| 4,668,413 | 5/1987 | Johnston et al. | 252/56 R |

OTHER PUBLICATIONS

Cadicamo et al., "A Second Study of Jojoba Oil, its Derivatives and other Cosmetic Oils", Soap, Cosmet., Chem. Spec., 59 (6), 36–8.

Shani, "Jojoba Oil and Some of its Derivatives in Cosmetic and Health Products", Soap, Cosmet., Chem. Spec., 59 (7), 42, 44.

Shani, "Functionalization at the Double-Bond Region of Jojoba Oil 3, Hydroxylic Derivatives", Ind. Eng. Chem. Prod. Res. Dev., 22 (1), 121–3.

Shani, "Functionalization at the Double-Bond Region of Jojoba Oil 1, Bromine Derivatives", J. Am. Oil Chem. Soc., 58 (9), 845–50.

Verbanic, "Jojoba: Answer to the Sperm Whale?," Chemical Business, Aug. 1986, pp. 30, 32.

*Primary Examiner*—William R. Dixon, Jr.
*Assistant Examiner*—E. McAvoy
*Attorney, Agent, or Firm*—Finnegan, Henderson, Farabow, Garrett & Dunner

[57] ABSTRACT

An Ethoxylated jojoba oil product and a method for making the same.

10 Claims, No Drawings

ETHOXYLATED JOJOBA OIL

BACKGROUND

This invention relates to an ethoxylated jojoba oil. It also relates to a method for producing ethoxylated jojoba oil.

Cosmetic and lubricant manufacturers are presently in need of an inexpensive replacement for sperm whale oil in their moisturizing and lubricating compositions. Jojoba oil, which is obtained from the crushed seeds of an evergreen desert shrub found in the southwestern United States and northern Mexico, has a chemical composition similar to that of sperm oil and it is used in many products as a substitute for sperm oil, such as transmission lubricants, high pressure lubricants, antifoam agents and cosmetic preparations. It is also used as a substitute for carnauba wax and beeswax. However, the current selling price of jojoba oil prohibits the application of the oil in many products despite the unique properties that the oil has to offer.

Prior to the present invention, it had been known to hydroxylate jojoba oil, and thereby form a slightly more hydrophilic product, through the use of acetic acid and hydrogen peroxide via the diepoxide. This process is described in the article by Arnon Shani entitled "Functionalization at the Double-Bond Region of Jojoba Oil, 3. Hydroxylic Derivatives," Ind. Eng. Chem. Prod. Res. Dev., 1983, vol. 22, p. 121–123. The process described by Shani has several problems associated with it. First, the acetic acid used in the process has a strong odor that remains with the hydroxylated product and makes it unsuitable for certain cosmetic uses. Second, the acetic acid does not decompose and must be neutralized or otherwise treated before the acetic acid can be disposed of. Furthermore, the hydroxylated product, while slightly more hydrophilic than jojoba oil, is not truly water soluble.

SUMMARY OF THE INVENTION

The present invention provides a new composition derived from jojoba oil that has all the advantageous properties of jojoba oil, but is water soluble so that this product can be used in diluted form while still taking advantage of the characteristic ester linkage.

The present invention also provides a method of making ethoxylated jojoba oil using a hydroxylation step that does not result in a smelly hydroxylated product or require a neutralization or other further treatment step. The invention also provides other advantages which will be more fully developed and inherent in the description of the invention.

The present invention then, relates to ethoxylated jojoba oil and, in particular, to an ethoxylated jojoba oil product that is a mixture of one or more compounds of the formulas:

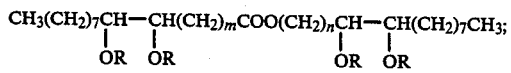
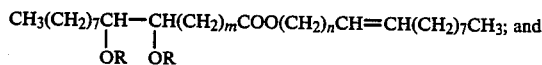
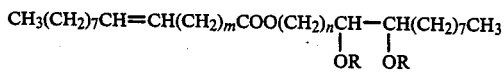

where $R=(-CH_2CH_2O-)_xH$; $m=7, 9, 11$ or $13$; $n=8, 10, 12,$ or $14$; and $x$ is an integer from $10-50$.

The invention also relates to a method for preparing an ethoxylated jojoba oil comprising:
(a) hydroxylating the jojoba oil by contacting the oil with formic acid and hydrogen peroxide to produce a hydroxylated jojoba oil; and
(b) ethoxylating the hydroxylated jojoba oil by contacting the hydroxylated jojoba oil with ethylene oxide.

DETAILED DESCRIPTION OF THE INVENTION

Jojoba oil is a colorless, odorless, waxy liquid. The formula for jojoba oil is believed to be as follows:

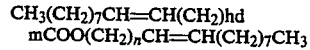

where m can have a value of 7, 9, 11 or 13 and n a value of 8, 10, 12 and 14. The distribution of values for m and n in jojoba oil are believed to be as follows: m is believed to be 7 in 7 to 11% of the oil; 9 in 69 to 71% of the oil; 11 in 13 to 17% of the oil; and 13 in 2 to 3% of the oil. n is believed to be 8 in 1 to 2% of the oil; 10 in 42 to 46% of the oil; 12 in 41 to 47% of the oil; and 14 in 7 to 8% of the oil. The above percentages are based on weight.

The first step in producing the inventive product is to react the jojoba oil with formic acid and hydrogen peroxide to form a hydroxylated jojoba oil which is a mixture containing one or more compounds of the following formulas:

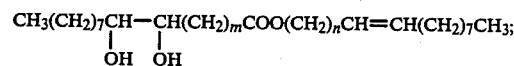
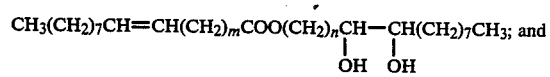
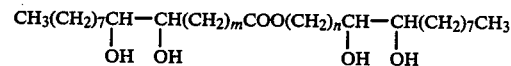

where m and n are defined as above.

The advantage of this hydroxylation step over prior hydroxylation steps is that the formic acid decomposes during the reaction process to form water and carbon monoxide as by-products of the process. This is not true of processes using acetic acid, which result not only in a smelly product, but also require a neutralization step after the hydroxylation reaction.

The molar ratio of jojoba oil to hydrogen peroxide can range from 1:1 to 1:6 and the molar ratio of jojoba oil to formic acid can range from 1:1 to 1:3. The concentration of hydrogen peroxide can range from 30–90% as an aqueous solution. Any suitable temperature can be used for this reaction. The lower the temperature, the slower the reaction. The preferred temperature ranges from about 50° C. to 150° C. The reaction generally takes place at atmospheric pressures.

The resulting products are hydroxylated jojoba oil, water and carbon monoxide. The conversion is essentially complete.

The hydroxylated jojoba oil can be recovered using conventional techniques for removing the water from the jojoba oil. A high purity hydroxylated jojoba oil can be obtained by stripping the residual formic acid and hydroqen peroxide using vaccuum distillation or evaporation or other similar processes.

The hydroxylated jojoba oil according to the present invention is then ethoxylated by contacting the hydroxylated jojoba oil with ethylene oxide.

This reaction is preferably accomplished in the presence of basic catalyst. This catalyst can be selected from sodium and potassium compounds such as sodium hydroxide, potassium hydroxide, sodium methoxide and the like.

The temperatures and pressures for the ethoxylation step can be varied over a wide range. Preferably, the reaction temperature ranges from about 50° C. to about 200° C. The reaction pressure is generally above atmospheric and preferrably up to about 100 p.s.i. The pressure is typically limited by the reaction vessel. The higher the pressure used, the faster the reaction will proceed.

The mole ratio of ethylene oxide to hydroxylated jojoba oil generally exceeds 1:1. Preferrably, the mole ratio of ethylene oxide to hydroxylated jojoba oil used in the reaction ranges from about 20–200 : 1. The thus formed ethoxylated jojoba oil is a mixture of at least one compound having the formulas believed to be as follows:

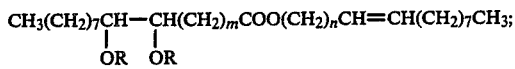

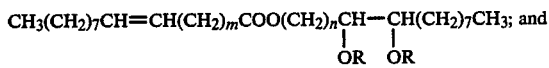

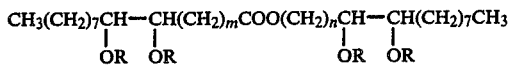

where R, m, n, and x are as defined above.

The ethoxylated jojoba oil is a water soluble compound that will blend into aqueous based cosmetics and moisturizers and yet maintain the desirable properties of jojoba oil. The material is also useful for lubrication products

EXAMPLES

Example I

Step (a)

Several samples of hydroxylated jojoba oil were prepared For each sample, 620 grams of jojoba oil and 76.5 grams of 90% formic acid were charged to a reactor and stirred. This mixture was heated to 90° C. To this mixture, 340 grams of 30% $H_2O_2$ were slowly added. This addition can be done in small increments or continuously and both methods were used in the various samples. The reaction was exothermic. The reaction temperature was allowed to rise to 110°-115° C. and was maintained at this temperature to digest for one hour. A vacuum was then applied to remove water. Each sample contained approximately 680 grams of hydroxylated product as a residue.

Step (b)

The residual acid in the hydroxylated product from step (a) was then neutralized. KOH, NaOH, NaOCH$_3$, and NaH were used in different samples of the hydroxylated product as a neutralizer. The neutralizer also functions as the catalyst. Vacuum and a nitrogen purge was then applied to remove any low boiling materials. The remaining product was then heated to 140°-150° C. and contacted with ethylene oxide with a hydroxylated product to ethlyene oxide ratio exceeding about 3:1. After digestion, a vacuum was applied to remove residue ethylene oxide. The remaining product was neutralized. Typical neutralization materials that were used in different samples include citric acid or phosphoric acid, etc.

Example II

Step (a)

Several samples of hydroxylate jojoba oil were prepared by mixing, in each sample, 620 grams of jojoba oil and 128 grams of 90% formic acid in a reactor and agitating the mixture. This mixture was heated to 90° C. To this mixture, 170 grams of 50% $H_2O_2$ were slowly added. Again, a strong exotherm resulted in which the reaction temperature rose to 110°-115° C. After the $H_2O_2$ addition, the mixture was allowed to digest for an hour at 110° C.-115° C. The reaction mixture was then neutralized with 25% NaOH to neutralize residual acid and to provide a catalyst for the ethoxylation step (b). Agitation was stopped and the phases were allowed to separate for an hour. The bottom aqueous layer was then drained off. The hydroxylated product was then vacuum dried.

Step (b)

The hydroxylated product was purged with nitrogen and then heated to 170° C. The ethoxylation step took place at 170 -180° C., contacting the hydroxylated product with ethylene oxide at a ratio of ethylene oxide to product greater that 1:1. After digestion, vacuum was applied to remove residue ethylene oxide. The resulting product was neutralized with lactic acid and added to an equal amount of water to make a 50% solution.

Example III

Hydroxylated jojoba oil samples as made from Example 1 (a) or Example II(a) were nitrogen purged. The samples were tested, and if necessary, treated to assure that the samples were free of residual acid. 120 Moles of ethylene oxide were added to one mole of hydroxylated jojoba oil using a methanolic potassium hydroxide catalyst. The resulting product, after neutralization of catalyst with citric acid, was a waxy solid which was completely soluble and formed a clear aqueous solution.

It will be apparent to those skilled in the art that various modifications and variations could be made in the invention without departing from the scope or spirit of the invention. The above examples of the invention are not to be construed as limitations to the invention.

We claim:

1. An ethoxylated jojoba oil.
2. An ethoxylated jojoba oil that is a mixture of one or more compounds of the formula:

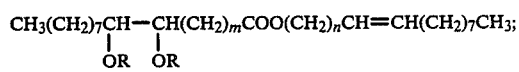

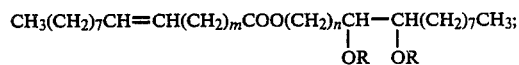

and

-continued

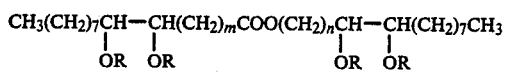

where R is $-(-CH_2CH_2O-)_x H$; m is 7, 9, 11, or 13; n is 8, 10, 12, or 14; and x is an integer ranging from about 10 to about 50.

3. A method for producing an ethoxylated jojoba oil comprising:
   (a) hydroxylating jojoba oil by reacting said oil with formic acid and hydrogen peroxide to produce a hydroxylated jojoba oil; and
   (b) ethoxylating said hydroxylated jojoba oil by reacting said hydroxylated jojoba oil with ethylene oxide.

4. The method according to claim 3 where in step (a) the molar ratio of jojoba oil to hydrogen peroxide ranges from 1:1 to 1:6 and the molar ratio of jojoba oil to formic acid ranges from 1:1 to 1:3.

5. The method according to claim 3 where the reaction temperature in step (a) ranges from about 50° to about 150° C.

6. The method according to claim 3 where in step (b) is conducted in the presence of a basic catalyst 7. The method according to claim 3 where in step (b) a potassium or sodium compound is used as said catalyst.

8. The method according to claim 7 where said catalyst is selected from sodium hydroxide, potassium hydroxide, and sodium methoxide.

9. The method according to claim 3 where the reaction temperature in step (b) ranges from about 50° to about 200° C.

10. The method according to claim 3 where in step (b) the molar ratio of ethylene oxide to hydroxylated jojoba oil ranges from 20:1 to 200:1.

* * * * *